Figure 1:

United States Patent [19]
Molina

[11] 4,176,205
[45] Nov. 27, 1979

[54] FINGERPRINT POWDER AND METHOD OF APPLICATION

[75] Inventor: Orlando G. Molina, Westminster, Calif.

[73] Assignee: Rockwell International Corporation, El Segundo, Calif.

[21] Appl. No.: 669,926

[22] Filed: Mar. 24, 1976

[51] Int. Cl.² .............................................. A61B 5/10
[52] U.S. Cl. ......................................... 427/1; 427/53; 427/1; 427/145; 427/157; 252/301.16; 156/241; 356/36; 252/1; 252/88; 252/408
[58] Field of Search ...................... 427/1, 53, 145, 157; 252/301.16

[56] References Cited

U.S. PATENT DOCUMENTS

| | | | |
|---|---|---|---|
| 2,066,535 | 1/1937 | Lucas | 427/1 |
| 2,986,831 | 6/1961 | Terek et al. | 427/1 X |
| 3,075,852 | 1/1963 | Bonora | 427/1 |
| 3,480,217 | 10/1968 | Obuchi | 427/1 X |
| 3,492,140 | 1/1970 | Honjo et al. | 427/1 |

*Primary Examiner*—Bernard D. Pianalto
*Attorney, Agent, or Firm*—Charles T. Silberberg; Max Geldin; L. Lee Humphries

[57] ABSTRACT

Fingerprint powder and method for developing latent fingerprints therewith, such powder comprised of a powder carrier, especially a mixture of silica and talc, containing a coloring agent, preferably a fluorescent dye. The fingerprint powder can be applied by blowing the powder over a surface containing latent fingerprints, or by brushing or pouring the powder on such surface, or by immersion thereof in such powder, thus developing and revealing a bright, sharp fingerprint, which can be photographed or lifted by applying tape or a strippable coating over the print.

19 Claims, 2 Drawing Figures

FINGERPRINT POWDER AND METHOD OF APPLICATION

BACKGROUND OF THE INVENTION

This invention relates to fingerprinting, and is particularly concerned with a novel fingerprint powder, particularly a fingerprint developing powder having high sensitivity, and to a method for developing or recording latent fingerprints employing such powder.

Various compositions and methods have heretofore been employed for developing or recording latent fingerprints. The conventional procedure for developing a latent fingerprint involves applying to the surface having such fingerprint thereon a small amount of a finely powdered solid material until the outline of the fingerprint becomes visible and then carefully spreading the applied powder over the fingerprint in order to bring out its pattern. Various substances including powdered metals such as aluminum and bronze, dragon's blood powder, a gray powder consisting of finely ground French chalk and mercury, and a black powder having a lampblack or charcoal base have been employed for this purpose.

However, the powder compositions heretofore employed have certain disadvantages. Of particular note, many of the prior art fingerprint powders are not sufficiently sensitive and do not provide the desired contrast to clearly bring out the fingerprint pattern, so that hand and fingerprints thus obtained lack clear visibility. Further, some of the prior art fingerprint powders have an abrasive action which tends to streak and/or obliterate the latent fingerprint when such powder is applied to the surface containing such fingerprint. Further, a brushing technique is generally employed with conventional powders, and development of fingerprints employing such prior art technique and powders is often difficult and time consuming, and requiring considerable skill, while at the same time avoiding waste by use of excess powder.

As exemplary of the prior art methods for fingerprint detection, are the following patents: U.S. Pat. No. 1,259,981 discloses the use of a powder for fingerprint detection containing a pigment and an adhesive. U.S. Pat. No. 3,132,036 discloses developing a latent fingerprint on a surface by applying to the surface a layer of opaque magnetizable powder and passing a magnet across the layer of powder. The patent also discusses the prior art use of iodine vapors for latent fingerprint detection. U.S. Pat. No. 3,075,852 discloses use of a powder for fingerprint detection, in admixture with a liquefied gaseous propellant.

In my copending application Ser. No. 649,293, filed Jan. 15, 1976, there is disclosed a dry powder indicator composition for detecting cracks and leaks in a component of a fluid-filled system, containing talc and silica as a carrier powder, and a coloring agent, which can be a fluorescent dye.

It is an object of the present invention to provide novel compositions and procedure for developing latent fingerprints on a surface. It is a particular object of the invention to provide a fingerprint powder which can be readily and rapidly applied to a surface containing latent fingerprints, without use of excess powder, and containing a coloring agent, such that the developer powder has high sensitivity, and to a method for rendering visible or detecting and developing either old or fresh latent fingerprints on a surface, employing such fingerprint powder, to obtain bright, sharp fingerprint patterns of high contrast and resolution.

DESCRIPTION OF THE INVENTION

I have found that the above objects can be accomplished according to the invention and an efficient sensitive fingerprint powder and a rapid economical method for detecting and developing fingerprints employing such powder can be provided by use of a fingerprint powder containing as carrier certain powder components, namely talc or silica, particularly in combination, together with a coloring agent, particularly certain fluorescent dyes.

It has been found that the oil and wax-like residues which are deposited by fingerprints or hand prints can be detected and their pattern sharply revealed by the use of the above noted fingerprint powder. During development of the fingerprint powder of the invention, it was found that formulations best suited for fingerprinting and which provided visible fingerprints having sharp contrast acted on the hand and finger residues deposited on surfaces by two different actions or mechanisms. Mechanism (a) is by adherence of the combination of inert carrier powders, notably a mixture of talc and silica, together with the coloring agent, particularly certain fluorescent dyes, to the oil-like or waxy-like fingerprint residues deposited on surfaces, especially the sealed surfaces of metal, glass, plastic or painted material. The second mechanism by which the fingerprint powder of the invention coacts with hand and finger residues deposited on surfaces, is by the actual dissolving action of the coloring agent, particularly fluorescent dye, with fingerprint residues of the more oily type. Functions (a) and (b) may occur or such actions proceed simultaneously or separately depending upon the degree of "oiliness" or "waxiness" left by the hand or fingerprints. However, both of these functions (a) and (b) are believed to occur only when certain types of dyes are employed, particularly certain naphthalimide dyes, and especially exemplified by the dye marketed as Morton Fluorescent Yellow G.

It is believed that the reason for this specific action with respect to the above fluorescent dyes is that they are exceptionally high in fluorescence when in the dry powdered state, in contrast to other dyes which are opaque or dull in color when exposed to fluorescent or black light illumination. Thus, dry powder formulations according to the invention containing the above noted naphthalimide type dyes as exemplified by Morton Fluorescent Yellow G, particularly when employed in combination with the above carrier powder of talc and silica, will provide highly brilliant fingerprints for very dry or old fingerprints as result of the high adherence of such formulation in contact with the surface containing the latent fingerprint, even in the absence of my actual dissolving action of the dye taking place due to the dryness and very small oily content, if any, of the latent fingerprint residue. In addition, such high sensitivity powder formulations containing these dyes can also react on fingerprints, e.g. of a relatively fresh nature, in any area thereof which offers sufficient liquidity or oiliness to dissolve the dye.

Thus, the invention provides a formulation or powder which is especially tailored for detecting and revealing fingerprint patterns, and which provide a double or dual action, namely, detection by adherence of the powder formulation containing both inert carrier and fluorescent dye powders, and by the highly sensitive dissolving action of the fluorescent dye, e.g. as exemplified by Morton Fluorescent Yellow G, to oily deposits from hand and/or fingerprints.

However, where other dyes which do not provide high fluorescence are incorporated into the inert carrier powder, particularly a combination of talc and silica, such fingerprint formulations, although not particularly suitable for detecting old or dry fingerprints, due to the absence of oiliness in such fingerprint residues, are affective in detecting fingerprints which provide sufficient oiliness to dissolve the dye.

A third unique function or characteristic of the invention composition is that because the formulations of the invention are so sensitive, fingerprints can be obtained simply by blowing the powder over the surface containing the hand or fingerprints, thus avoiding the tedious operation of "brushing" which is the usual method of application of conventional fingerprint powders, e.g. as used in criminology. However, the fingerprint formulation of the invention can be applied to surfaces containing fingerprints, if desired, by brushing or pouring the powder onto the surface, or by immersing the surface containing the latent fingerprints in the formulation.

As previously noted, it is particularly desirable that the carrier powder employed in the fingerprint powder formulation of the invention have good adherence to even a small amount of oily or waxy fingerprint residues, particularly in combination with the powdered coloring agent or dye incorporated therein. It has been found for this purpose that talc, silica, and particularly mixtures thereof, are eminently suited for this purpose. Other conventional inert powders such as diatomaceous earth have been tried as carrier powders for the fingerprint formulation of the invention, but were found to be unsuitable in achieving the proper adherence to the fingerprint residues, when employed in combination with a coloring agent or dye.

Generally there can be employed about 25 to about 95%, usually about 50 to about 90% of dry powder carrier, and about 5 to about 75%, usually about 10 to about 50%, of dry coloring agent or dye, by weight of the total fingerprint powder. As previously noted, it has been found that most effective results are achieved employing a combination of talc and silica, particularly in the proportions noted below, in combination with a coloring agent or dye.

The talc component of the fingerprint composition is a fine white powder of small but irregular particle size. A commercially available material particularly suitable for purposes of the invention is that marketed as Desertalc Mikro 507, by Desert Minerals, Inc. of Los Angeles, Calif. The latter material is a semi-tremolitic-acicular-platey having a particle size distribution ranging from about 15 to less than 1 micron, and is essentially a calcium-magnesium silicate. This white powder provides a unique combination of highly irregular particle sizes and shapes, leaving an almost invisible adherent film deposit of microsize particles on the surface to which the composition is applied. Such fine powdery talc adheres to almost any type of surface including paper, wood, metal, plastic, glass, ceramic and painted surfaces. Other suitable talcs include Desertalc Mikro 706, 707 and 906. Desertalc Mikro 706 and 707 are ultra-fine micaceous particle structures of thin, soft translucent plates. Desertalc Mikro 906 is a steatic-platey, spherical material having a structure of fine small plateles and spheres of high uniformity. This material is low in carbonate and is non-abrasive. Particle sizes of Desertalc 706, 707 and 906 are similar to 507, ranging from 15 to less than 1 micron.

The above described talcs, illustrated by Desertalc Mikro 507, 706, 707 and 906 have a different structure from conventional talc.

The second component of the preferred fingerprint powder carrier is silica, employed also preferably in fine powder form of particle size ranging from about 0.007 and about 0.050 micron (about 70 to about 500 Angstroms), and is an extremely fluffy, snow-white powder of extremely low bulk density. A commercially available form of this component is marketed as Cab-O-Sil M-5 by Cabot Corporation. The Cab-O-Sil has an enormous external area, one gram of Cab-O-Sil M-5 having about 400 square meters of surface area. Cab-O-Sil M-5 is a submicroscopic fire-dry fumed silica different in structure from precipitated silicas or silica gels or aerogels. This white silica powder imparts free-flowing, non-caking properties to the overall fingerprint powder composition, and also aids in developing bright fluorescent indications from fluorescent dyes.

It has been found that in order to obtain most effective results with the fingerprint composition of the invention, when employing a combination of talc and silica, the components thereof should be employed in certain proportions. Thus, the talc component is generally employed in an amount ranging from about 5 to about 60%, preferably from about 25 to about 50%, and the silica component generally in an amount ranging from about 15 to about 75%, preferably from about 25 to about 60%, by weight of the overall composition, including the dry powder dye.

Dyes or coloring agents which are particularly suited for use in the fingerprint compositions hereof are those which in the dry powder state, as previously noted, have high brightness or fluorescence, and preferably also have good adherence to surfaces containing fingerprint residues. Such coloring agents or dyes are particularly valuable for use in the invention composition since the resulting fingerprint compositions provide highly brilliant fingerprint patterns for old or dry latent fingerprints which have very little remaining oily residues, as result of the brilliance of the dye in its powdered form, as well as for relatively fresh latent fingerprints containing oily residues and wherein the dye functions to provide brilliant indications by dissolving in such oily residues.

Preferred dyes which have this dual function are certain fluorescent naphthalimide dyes of which the dye Morton Fluorescent Yellow G, Color Index 75, is particularly effective. Other fluorescent dyes such as the coumarin dyes as represented by Calcofluor White RW, Color Index-Fluorescent brightening agent 68, can be employed effectively for this purpose alone or in combination with the above naphthalimide dyes, particularly Morton Fluorescent Yellow G.

Other fluorescent naphthalimide dyes which can be employed include, for example, the dye marketed as Fluorol 7GA, Color Index-Fluorescent brightening agent 75; Calcofluor Yellow, Color Index-Fluorescent brightening agent No. 4; and Azosol Brilliant Yellow 6 GF, Color Index - Solvent Yellow 44. Other fluorescent coumarin dyes which can be employed include, for example, Blancophor White AW, Color Index-Fluorescent brightening agent 68. Still other fluorescent dyes which can be employed include Rhodanine B, Rhodanine 6 GDN, Auramine and Eosine G. However, these dyes are not as effective for obtaining bright and sharp fingerprint patterns of old or dry latent fingerprints as for example, are obtained with Morton Fluorescent Yellow G, Calcofluor White RW, or combinations thereof.

Non-fluorescent fingerprinting compositions can also be obtained according to the invention, employing non-fluorescent or daylight type dyes such as azo type dyes, e.g., xylenaezo-beta-naphthol, Mefford No. 322 dye, believed to be o-tolueneazoxyleneazo-beta-naphthol, and the azo dyes marketed as Oil Red "O" and Sudan Red "O." These dyes conveniently can be employed where daylight or white light is only available. However, it is preferred to employ fluorescent dyes having greater sensitivity or detectability as result of the high contrast obtained by the fluorescent indications.

Further, instead of employing fluorescent or non-fluorescent dyes as colorants or coloring agents in the above carrier powders, inorganic or organic pigments can be employed. Thus, non-fluorescent fingerprint powders can be obtained by employing the inert powders talc, e.g. Desertalc Mikro 705, or silica, e.g. Cab-O-Sil M5, or mixtures thereof, with suitable amounts of graphite or finely ground aluminum pigment, such as the material marketed as Aluminum Pigment Extra Fine Lining Powder No. 422, marketed by Aluminum Co. of America (Alcoa). Such non-flourescent fingerprinting formulations have been found superior to current fingerprinting powders employed in criminology and containing similar graphite or aluminum powders, due to the talc and silica powders employed as carrier in the invention compositions. Molybdenum disulfide can also be employed as pigment. Graphite and molybdenum disulfide can be used effectively on surface or areas which are light colored to obtain a contrasting dark fingerprint pattern. In places where darkness prevails, the aluminum pigmented powder is particularly effective. The aluminum, graphite and molybdenum disulfide pigment powders employed are preferably of microsize particle range, e.g. of about 0.7 micron size.

Other inorganic or organic pigments, either fluorescent or non-fluorescent, can also be employed as indicating material in the fingerprint composition of the invention, examples of fluorescent pigments being the materials marketed as "Dayglow" fluorescent pigments, zinc sulfide or chrysene, fluorescent emerald green, and the like, and examples of non-fluorescent pigments being metallic oxides, cobalt blue and "Permansa" red.

The amount of dye or pigment, or mixtures thereof, which is incorporated into the dry powder carrier to produce the fingerprint powder composition of the invention can range from about 5 to about 75%, preferably about 10 to about 50%, by weight, based on the total or overall weight of the dry fingerprint position, particularly employing a combination of talc and silica as carrier. In preparing fingerprint compositions employed in the invention, the dye or pigment, or mixtures thereof, is simply added to the powder carrier, e.g. mixture of talc and silica, in the desired proportions.

Typical fingerprint powders containing a coloring agent or dye which can be employed in the invention process are set forth in Tables I and II below, Table I being directed to fluorescent fingerprint powders and Table II to non-fluorescent fingerprint powders.

TABLE I

| Material Name | Fluorescent Fingerprint Powder Percentage by Weight | | | | | | | | |
|---|---|---|---|---|---|---|---|---|---|
| | A | B | C | D | E | F | G | H | I |
| Desertalc Mikro 507 | 25 | 25 | 25 | 25 | 50 | — | — | 50 | 10 |
| Cab-O-Sil M5 | 60 | 50 | 45 | 25 | — | 50 | 65 | 25 | 60 |
| Morton Fluorescent Yellow G Dye | 15 | 25 | 30 | 50 | 50 | 50 | 35 | 25 | 30 |
| Totals | 100 | 100 | 100 | 100 | 100 | 100 | 100 | 100 | 100 |

TABLE II

| Material Name | Nonfluorescent Fingerprint Powder Percentage by Weight | | | | | | | | |
|---|---|---|---|---|---|---|---|---|---|
| | J | K | L | M | N | O | P | Q | R | S |
| Desertalc Mikro 507 | 25 | 10 | — | — | 25 | 10 | — | — | — | 40 |
| Cab-O-Sil M5 | 60 | 20 | 30 | 30 | 60 | 20 | 60 | 60 | 50 | 40 |
| Aluminum Powder Pigment | 15 | 70 | 70 | — | — | — | — | 40 | 25 | 10 |
| Graphite or Molybdenum disulfide powder | — | — | — | 70 | 15 | 70 | 40 | — | 25 | 10 |
| Totals | 100 | 100 | 100 | 100 | 100 | 100 | 100 | 100 | 100 | 100 |

Fingerprint powders B and D of Table I above have been found particularly effective fluorescent powders. Fingerprint powders K and N of Table II are highly effective non-fluorescent fingerprint powders.

As previously noted, the fingerprint powder of the invention can be employed simply by blowing the powder over a surface having a latent fingerprint thereon to distribute the powder uniformly on the surface, in order to expose the developed fingerprint. The latent fingerprint is rapidly developed, and the pattern thereof can be viewed in fluorescent or black light where a fluorescent dye or pigment is employed, or in ordinary daylight where a non-fluorescent dye or pigment is used in the fingerprint powder. If desired, and as previously pointed out, the fingerprint powder can also be applied by conventional brushing, pouring or immersing-in-the powder techniques. The procedure of the present invention for developing, detecting and viewing fingerprints employing the fingerprint composition of the invention can be carried out rapidly and easily, permitting even unskilled operators to obtain excellent fingerprints.

The fluorescent powders of the invention provide fingerprints, hand prints, and the like, which can be photographed under black light or daylight illumination, or "lifted." Such prints can be "lifted" using tape such as masking tape or by spraying strippable lacquers or vinyls onto the developed fingerprint. Such strippable coatings can have an organic polymer base comprised, for example, of vinyls, acrylics, nitrocellulose, butyrates, and latex, the vinyl polymers and copolymers, such as vinyl chloride resin and vinyl chloride-vinyl acetate copolymers, being particularly useful. Such coating composition includes a volatile solvent, and can also contain a plasticizer such as dioctyl phthalate as an optional component. An effective strippable coating for purposes of the present invention can comprise about 19% polyvinyl chloride or vinyl chloride-vinyl acetate-polymer, about 61% toluene, 14% methyl ethyl ketone and about 6% diisooctyl phthalate, providing a clear coating.

As previously noted, the stripped coating containing the developed fingerprint, a "lifted" tape containing the developed fingerprint or the developed fingerprint on the surface initially containing the latent fingerprint can be photographed under black light illumination where the powder contains a fluorescent dye or pigment, or in daylight where the powder contains a non-fluorescent colorant.

Illustrative examples of practice of the invention are set forth below.

EXAMPLE 1

The fluorescent fingerprint powder, composition B in Table I, was blown over a metal surface containing a latent fingerprint. Excess powder was removed during this procedure, the powder remaining on the surface being that which adhered to the residue of such latent fingerprint.

The developed fingerprint was detected and viewed under fluorescent illumination, showing a sharp, bright yellow fingerprint pattern as revealed by the fluorescent indications of the fingerprint powder adhered to the latent fingerprint, against the surface background.

FIG. 1 of the drawing shows a slightly magnified photograph of the fingerprint taken directly from the powder-treated surface according to this example. The photograph shows the high contrast and resolution of the fingerprint pattern produced employing the fingerprint powder of the invention.

Figure 2:

FIG. 2 of the drawing is a magnified detail of the same print taken directly from the powder-treated surface containing the fingerprint pattern.

No negative was employed in obtaining the photograph in either FIG. 1 or FIG. 2, the recording the fingerprint pattern. A Polaroid film-loaded camera with a yellow filter and black light illumination, as noted above, were employed for obtaining quick results.

EXAMPLE 2

The procedure of Example 1 is repeated, but applying the fingerprint powder composition B to a surface containing an old latent fingerprint about 20 days old.

Results obtained are similar to those obtained in Example 1, the fingerprint powder B still producing a sharp, bright fingerprint pattern of high contrast, from the old fingerprint.

EXAMPLE 3

The procedure of Example 1 is repeated, but employing fingerprint powder composition D of Table I instead of fingerprint powder B.

Results similar to those of Example 1 are obtained.

EXAMPLE 4

The procedure of Example 1 is repeated, but employing fingerprint powder composition N of Table II in place of fingerprint powder B.

In this case however the fingerprint pattern developed is not photographed, but rather is viewed in ordinary daylight, revealing a dark fingerprint pattern of good contrast, against a light colored background.

EXAMPLE 5

The procedure of applying the fingerprint powder to a surface containing a latent fingerprint, as in Example 1, is followed, employing instead, composition E of Table 1.

The resulting fingerprint is viewed under fluorescent light to reveal a bright fingerprint pattern of good resolution.

EXAMPLE 6

The procedure of Example 1 is repeated, and after the fingerprint powder B is applied, a strippable clear vinyl coating comprised of about 19% polyvinyl chloride, about 61% toluene, 14% methyl ethyl ketone and about 6% diisooctyl phthalate is applied and the coating permitted to dry. The coating is then strippd from the surface and photographed to reveal a bright clear fingerprint pattern similar to that shown in FIGS. 1 and 2 of the drawing.

From the foregoing, it is seen that the invention provides a simple, rapid and economical procedure for readily detecting or developing latent fingerprints, employing a fingerprint developing powder containing as inert carrier powder, talc or silica, particularly a combination thereof, and incorporating a dry coloring agent or colorant, particularly a dry fluorescent powder, which in conjunction with the above inert carrier, is particularly adherent to the oily or waxy residues of the latent fingerprint, and is also effective in developing old or "dry" latent fingerprints, to provide sharp colored fingerprint patterns, either under fluorescent or daylight conditions.

Although the invention has been described chiefly in relation to fingerprints, it will be understood that the invention is equally effective for detecting and developing hand prints, and the term "fingerprint" or "print" as employed herein is intended to encompass hand prints as well as fingerprints.

While I have described particular embodiments of my invention for the purpose of illustration within the spirit of the invention, it will be understood that the invention is not to be taken as limited except by the scope of the appended claims.

What is claimed is:

1. A method for detecting or developing a latent fingerprint on a surface, which comprises applying to said surface a composition comprising a carrier powder selected from the group consisting of talc and silica, and mixtures thereof, and a coloring agent capable of forming a colored pattern of the fingerprint in conjunction with said carrier powder, said coloring agent being a fluorescent dye, and viewing said surface containing the developed fingerprint under lighting conditions to obtain a colored fluorescent fingerprint pattern.

2. A method as defined in claim 1, said dye being a fluorescent naphthalimide dye.

3. A method as defined in claim 2, said carrier powder consisting essentially of a mixture of about 25 to about 50% talc and about 25 to about 60% silica, and said coloring agent being present in an amount ranging from about 10 to about 50%, by weight of the total composition.

4. A method as defined in claim 1, said fluorescent dye selected from the group consisting of Morton Fluorescent Yellow G, Color Index 75, and Calcofluor White RW, Color Index - Fluorescent brightening agent 68, and mixtures thereof.

5. A method as defined in claim 4, said carrier powder consisting essentially of a mixture ranging from about 5 to about 60% talc and about 15 to about 75% silica, and said coloring agent being present in an amount ranging from about 5 to about 75%, by weight of the total composition.

6. A method as defined in claim 1, said carrier powder consisting essentially of a mixture ranging from about 5 to about 60% talc, and about 15 to about 75% silica, and said coloring agent being present in an amount ranging from about 5 to about 75%, by weight of the total composition.

7. A method as defined in claim 6, including applying tape or a strippable coating to the developed fingerprint and lifting said tape or stripping said coating containing said developed fingerprint from said surface, including photographing the developed fingerprint on said lifted tape or on said stripped coating.

8. A method for detecting or developing a latent fingerprint on a surface, which comprises applying to said surface a composition comprising a carrier powder and a coloring agent capable of forming a colored pattern of the fingerprint in conjunction with said carrier powder, said coloring agent being selected from the group consisting of fluorescent and non-fluorescent dyes and pigments, said carrier powder consisting essentially of a mixture ranging from about 5 to about 60% talc and about 15 to about 75% silica, and said coloring agent being present in an amount ranging from about 5 to about 75%, by weight of the total composition, and viewing said surface containing the developed fingerprint under lighting conditions to obtain a visible colored fingerprint pattern.

9. A method as defined in claim 8, said carrier powder consisting essentially of a mixture of about 25 to about 50% talc and about 25 to about 60% silica, and said coloring agent being present in an amount ranging from about 10 to about 50%, by weight of the total composition.

10. A fingerprint developing powder composition consisting essentially of talc in an amount ranging from about 5 to about 60%, silica in an amount ranging from about 15 to about 75%, and a coloring agent selected from the group consisting of fluorescent and non-fluorescent dyes and pigments, in amount ranging from about 5 to about 75%, by weight.

11. A composition as defined in claim 10, consisting essentially of talc in an amount ranging from about 25 to about 50%, silica in an amount ranging from about 25 to about 60%, and a coloring agent in an amount ranging from about 10 to about 50%, by weight.

12. A composition as defined in claim 11, wherein said coloring agent is a fluorescent dye.

13. A composition as defined in claim 10, wherein said coloring agent is a fluorescent dye.

14. A composition as defined in claim 13, said fluorescent dye being a fluorescent naphthalimide dye.

15. A composition as defined in claim 13, said fluorescent dye being selected from the group consisting of Morton Fluorescent Yellow G, Color Index 75, and Calcofluor White RW, Color Index - Fluorescent brightening agent 68, and mixtures thereof.

16. A composition as defined in claim 15, consisting essentially of talc in an amount ranging from about 25 to about 50%, silica in an amount ranging from about 25 to about 60%, and a coloring agent in an amount ranging from about 10 to about 50%, by weight.

17. A composition as defined in claim 15, wherein the particle size of said talc ranges from about 15 to less than 1 micron, said silica being fumed silica of low bulk density and having a particle size ranging from about 0.007 to about 0.050 micron.

18. A composition as defined in claim 10, wherein the particle size of said talc ranges from about 15 to less than 1 micron, said silica being fumed silica of low bulk density and having a particle size ranging from about 0.007 to about 0.050 micron.

19. A composition as defined in claim 10, wherein said talc is a semi-tremolitic-acicular-platey in the form of a white powder of irregular particle sizes and shapes, leaving an almost invisible film deposit.

* * * * *